United States Patent [19]

Kanai et al.

[11] Patent Number: 4,931,036
[45] Date of Patent: Jun. 5, 1990

[54] INTRA-AORTIC BALLOON PUMP

[75] Inventors: Naritoshi Kanai, Tokyo; Akira Suzuki, Nishio, both of Japan

[73] Assignee: Aisin Seiki Kabushiki Kaisha, Aichi, Japan

[21] Appl. No.: 170,201

[22] Filed: Mar. 18, 1988

[30] Foreign Application Priority Data

Mar. 18, 1987 [JP] Japan ..................................... 62-838

[51] Int. Cl.⁵ ........................................... A61M 29/02
[52] U.S. Cl. ...................................... 600/18; 604/99; 604/282
[58] Field of Search ...................... 600/18; 604/96, 97, 604/98, 99, 282, 283

[56] References Cited

U.S. PATENT DOCUMENTS

| 3,504,662 | 4/1970 | Jones | 600/18 |
| 4,327,709 | 5/1982 | Hanson et al. | 600/18 |
| 4,362,150 | 12/1982 | Lombadi et al. | 600/18 |
| 4,515,587 | 5/1985 | Schiff | 600/18 X |
| 4,531,512 | 7/1985 | Wolvek et al. | 600/18 |
| 4,535,757 | 8/1985 | Webster | 600/18 |
| 4,546,759 | 10/1985 | Solar | 600/18 |

Primary Examiner—Max Hindenburg
Assistant Examiner—John P. Lacyk
Attorney, Agent, or Firm—Sughrue, Mion, Zinn, Macpeak & Seas

[57] ABSTRACT

A retardation in the deflating motion of a balloon caused by a local collapse thereof is prevented. A tubular sleeve having a multiplicity of small apertures in the periphery therein is disposed for axial movement between the internal spaces of the balloon and a catheter. In use, the sleeve is inserted into the catheter to prevent a fluid channel from being blocked upon occurrence of a local collapse of the balloon. To facilitate positioning the sleeve, a projection is formed on an elongate stylet adjacent to its distal end to apply a braking action to the sleeve and secure it in place when the latter reaches a given position within the balloon.

12 Claims, 4 Drawing Sheets

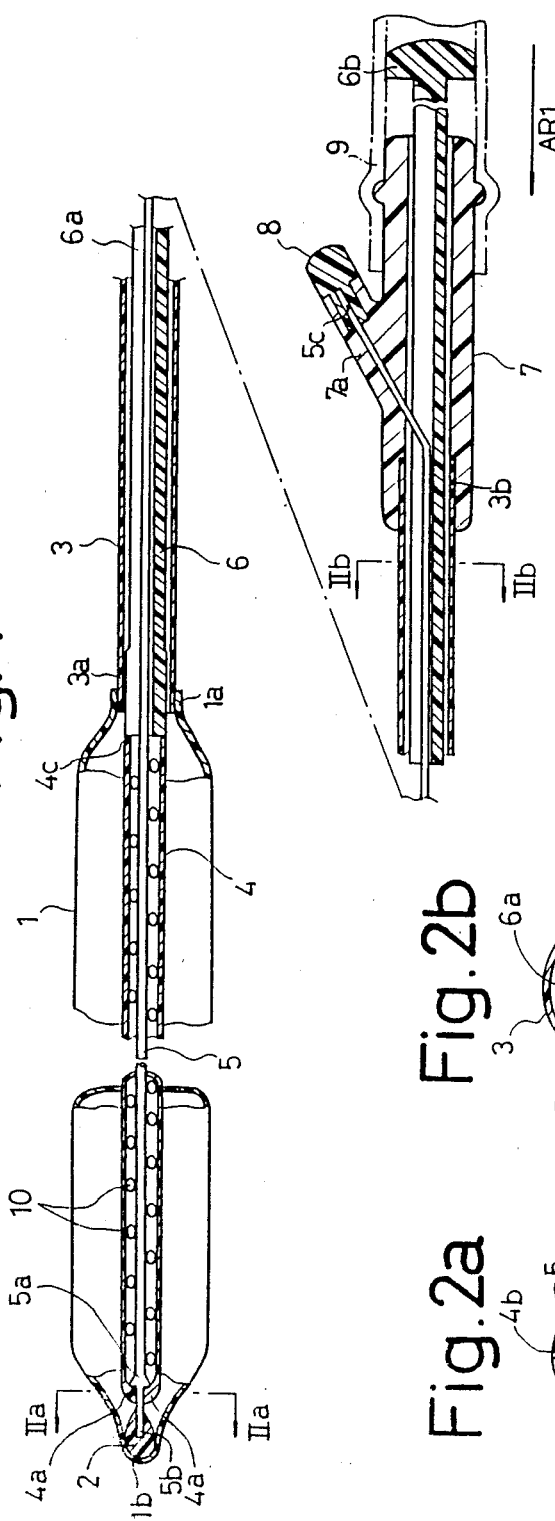

Fig. 3a PRIOR ART
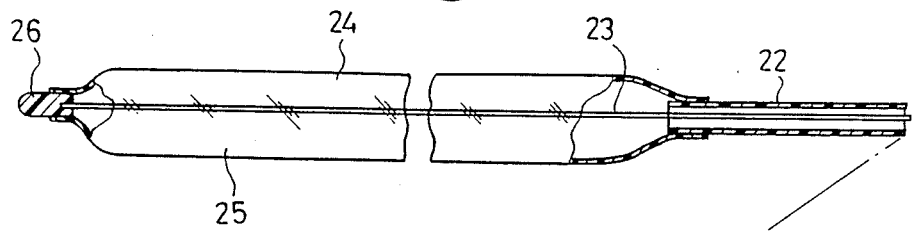
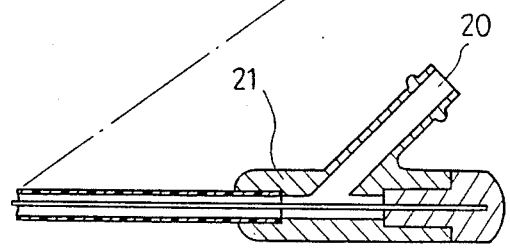
Fig. 3b PRIOR ART
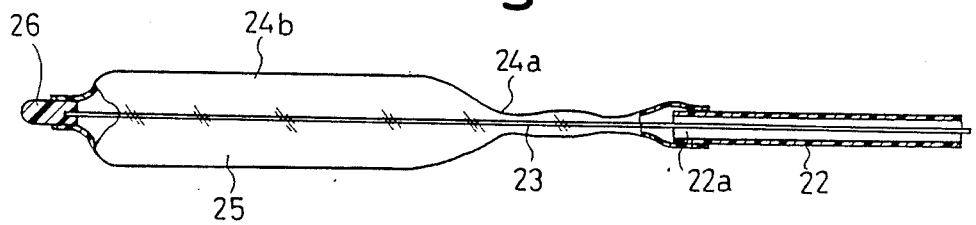

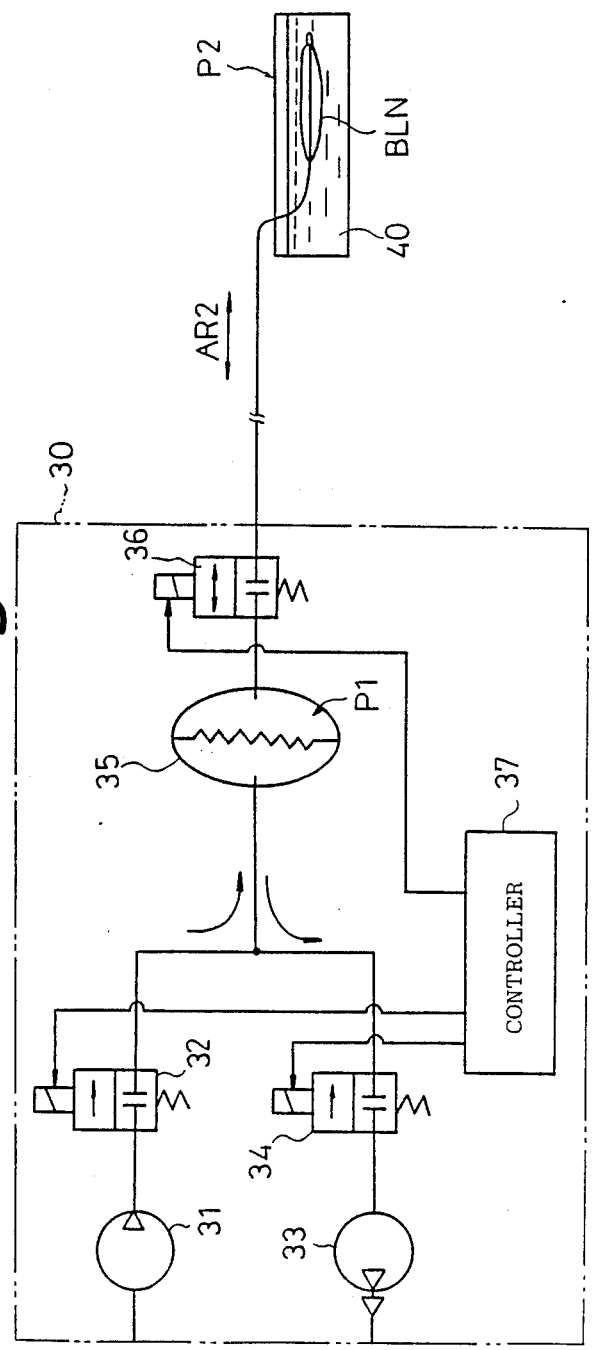

INTRA-AORTIC BALLOON PUMP

BACKGROUND OF THE INVENTION

The invention relates to an intra-aortic balloon pump which is inserted into the aorta of a patient to assist in the functioning of a heart.

The art relating to such intra-aortic balloon pump is disclosed in U.S. Pat. No. 4,327,709, U.S. Pat. No. 4,362,150 and U.S. Pat. No. 4,422,447, for example. Known intra-aortic balloon pumps can be categorized into a surgical type and a percutaneous type. A relatively thick tube is present inside the balloon of the former type, which therefore cannot be folded into a smaller configuration, and hence a surgical operation is required to insert it into the aorta of a patient. A balloon pump of the latter type can be reduced in its profile by folding or wrapping it, and thus can be inserted into the aorta without requiring a surgical operation. This simplifies the handling of a balloon pump of percutaneous type during its mounting and dismounting in a preferable manner.

One example of an intra-aortic balloon pump of the percutaneous type is illustrated in FIG. 3a. In this Figure, one end of a balloon 24 is connected to one end of a tubular member (catheter) 22 to provide a communication between the internal spaces of the both members. The other end of the balloon 24 is supported by one end of a central wire 23 which is disposed within the member 22. The internal space of the member 22 is in communication with a drive port 20. Accordingly, a desired drive unit may be connected to the port 20 to apply a positive and a negative pressure thereto alternately, thus enabling the balloon 24 to inflate and deflate alternately and repeatedly. Thus, when a positive pressure is applied, a drive fluid such as helium gas, for example, passes through the internal space of the member 22 to enter the balloon 24, the internal space of which is expanded, thus expanding or inflating the balloon. In response to the application of negative pressure, the drive fluid within the balloon 24 is displaced therefrom through the member 22 to flow out of the port 20, thus deflating the balloon 24. A poor functioning heart can be assisted by performing such inflating and deflating motion in synchronism with the beating motion of the heart of a patient.

In an intra-aortic balloon pump as illustrated in FIG. 3a, it is to be noted that during its deflating motion, the balloon 24 tends to begin its deflation in a region adjacent to a catheter opening 22a earlier than the distal end thereof, as illustrated in FIG. 3b. It will be noted that the balloon 24 requires a further deflating motion under the condition illustrated in FIG. 3b. However, the contraction of part of the balloon 24 reduces the fluid channel providing a communication between the internal space of the balloon 24 and the catheter opening 22a, thereby standing in the way of the effluence of the fluid. Accordingly, such phenomenon tends to retard the deflating motion of the balloon.

This phenomenon has been observed using an experimental apparatus illustrated in FIG. 4a which is used to determine a change occurring in the pressure. An intra-aortic balloon pump is shown at BLN which is driven by a drive unit 30. In order to load the balloon pump BLN, it is immersed into a water vessel 40. The drive unit 30 comprises a compressor 31 which produces a positive pressure, a vacuum pump 33 which produces a negative pressure, solenoid valves 32, 34, an isolator 35 and a controller 37. The drive unit 30 is designed to produce a positive and a negative pressure alternately, whereby there occurs a movement of a fluid in a direction indicated by a double-headed arrow AR2 within a tube which interconnects the drive unit 30 and the balloon pump BLN.

FIG. 4b graphically shows a secondary pressure P1 of the isolator and a pressure P2 which prevails within the balloon pump, both of which are obtained using the arrangement mentioned above. In FIG. 4b, a systole is indicated at T1 and a diastole is shown at T2. During the systole, the balloon pressure P2 should theoretically change with a constant decline as indicated by broken lines, but in actuality, the rate of decline is reduced at a point where the pressure has been reduced to one-half the initial value, thus retarding a reduction in the pressure. It is considered that this is caused by the contraction of part 24a of the balloon to reduce the fluid channel between the balloon and the central wire 23, presenting an increased resistance to the flow of fluid in such region.

Such retardation of the inflating motion is inherent in the construction of the percutaneous balloon. In a balloon of the surgical type, a portion thereof which corresponds to the central wire is formed by a relatively thick, hollow member having a multiplicity of openings in its periphery which permit a fluid flow. Accordingly, a balloon pump of surgical type does not suffer from a restricted effluence of fluid from the rest of the balloon due to the contraction of part thereof which occurs first. However, it is of course recognized that a surgical operation of a patient is required to use a balloon pump of surgical type.

The purpose of an intra-aortic balloon pump is to assist in the pulsation of a heart by causing the balloon to deflate with a timing which is determined by the pulsation of the heart to reduce the blood pressure within the aorta. However, when the heart rate increases to an abnormally high value, or an unpredictable pulsation occurs due to the arrhythmia, a failure of the balloon to deflate rapidly causes the likelihood that the presence of the balloon itself may interfere with the pulsation.

An approach which accommodates for such difficulty is disclosed in U.S. Pat. No. 4,515,587 wherein a corrugated resilient member is disposed between the internal spaces of the catheter and the balloon in a displaceable manner so that when inserted into the balloon, the resilient member prevents a local collapse of the balloon during its deflating motion. However, this still involves the following difficulties:

1. When the resilient member is expelled into the balloon from the catheter tube, it is located within a patient and hence is invisible by an operator, who therefore must rely on his experience and skill in positioning the resilient member. Thus, a balloon pump of this kind requires a high level of skill and is very difficult to operate.

2. It is necessary to expel the resilient member into the balloon from the catheter tube immediately after the balloon pump has been inserted into the physical body of a patient, and to remove the resilient member from the balloon into the catheter tube before the balloon pump is to be removed. Thus, the mounting and dismounting operation of the balloon pump is troublesome and requires an extended length of time.

SUMMARY OF THE INVENTION

It is an object of the invention to provide an intra-aortic balloon pump which avoids the need for a surgical operation on a patient for its mounting, which provides a rapid deflating motion and which is easy to operate.

The above object is accomplished in accordance with the invention by providing a displaceable sleeve member axially extending within a balloon pump and formed with a fluid passage therethrough. It will be noted that a restriction in the effluence of the fluid occurred in the intra-aortic balloon pump shown in FIG. 3a when the balloon deflates locally because there has been only one fluid passage which interconnects the balloon and the catheter. Accordingly, a tubular member is provided in surrounding relationship with the central wire and has a multiplicity of openings in its periphery which communicate each other through the internal space permit an effluence, when a part of the balloon has locally deflated, of the remaining fluid through the internal space of the tubular member. Such tubular member will be of an increased diameter, which results in an increased outer diameter of the resulting balloon, if it is folded, thus standing in the way to inserting it into the physical body of a patient without a surgical operation. However, in accordance with the invention, the sleeve member is displaceable in the axial direction. When the sleeve member is brought to its retracted position toward the catheter, only a thin member such as a central wire is left within the internal space of the balloon, which therefore can be wrapped or folded to reduce its profile. Accordingly, the balloon under this condition may be inserted into the physical body of a patient in a similar manner as a conventional percutaneous balloon without requiring a surgical operation. After the balloon pump has been inserted into the physical body of a patient and restored to its original configuration, the sleeve member may be expelled into the internal space of the balloon. Once the sleeve member is lodged into the internal space of the balloon, an effluence of a fluid within the balloon through the internal space of the sleeve member is permitted, thus preventing any interference with the effluence of the fluid if a local deformation of the balloon occurs.

In accordance with the invention, special positioning means is provided to facilitate a positioning of the sleeve member.

Other objects and features of the invention will become apparent from the following description of an embodiment thereof shown in the drawings.

BRIEF DESCRIPTION OF THE DRAWINGS

FIG. 1 is a longitudinal section of an intra-aortic balloon pump according to one embodiment of the invention;

FIGS. 2a and 2b are cross sections taken along the lines IIa–IIa and IIb–IIb shown in FIG. 1;

FIGS. 3a and 3b are front views of conventional intra-aortic balloon pump of percutaneous type;

FIG. 4a is a block diagram of an experimental apparatus; and

FIG. 4b is a timing chart illustrating changes occurring in the pressure waveforms determined with the apparatus shown in FIG. 4a.

DETAILED DESCRIPTION OF PREFERRED EMBODIMENT

Figure 4B:
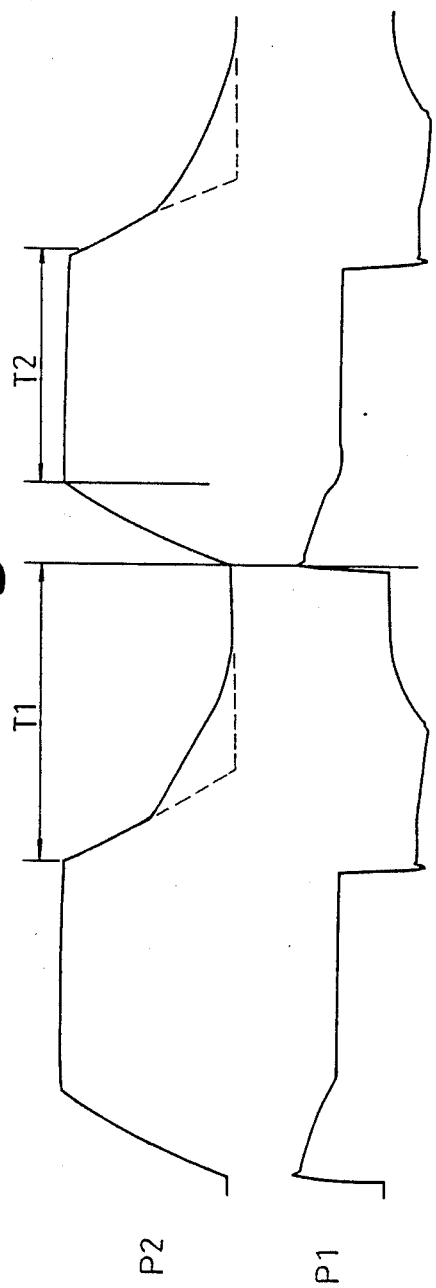

FIG. 1 shows a longitudinal section of an intra-aortic balloon pump according to one embodiment of the invention, and FIGS. 2a and 2b show cross sections, taken along the lines IIa–IIa and IIb–IIb shown in FIG. 1, to an enlarged scale. Referring to FIG. 1, a balloon 1 is in the form of a bag having a substantially cylindrical configuration, and is formed of a thin polyurethane film. At its one end, the balloon 1 is formed with an opening 1a which is secured to the outer peripheral surface of a catheter 3 at its one end 3a. A hermetic seal is achieved in the bond between the balloon 1a and the catheter 3a. The catheter 3 is cylindrical in configuration having an internal diameter of about 3 mm, and is formed of polyurethane. At its other end 3b, the catheter 3 is coupled to a Y-shaped connector 7. A central wire 5 is disposed along the center axis of the catheter 3 within its internal space. The wire 5 is formed of a stainless steel and has a diameter of about 0.5 mm. A tip 2 of polyurethane is secured to one end 5b of the wire 5. The balloon 1 has its other end 1b disposed in surrounding relationship with the tip 2, with the end 1b being secured to the tip 2. Accordingly, the balloon end 1b is supported by the wire 5 through the tip 2.

A sleeve 4 and an insertion member 6, both formed of polyethylene, are disposed in surrounding relationship with the central wire 5. Both the sleeve 4 and the member 6 have external diameters of about 2.5 mm, and thus is slightly less than the internal diameter of the catheter 3. The sleeve 4 is cylindrical in configuration, and a multiplicity of apertures 10 are formed around its entire periphery at a given pitch extending through the wall thereof. Each of apertures 10 has a diameter of about 1.5 mm.

At its end 4c adjacent to the insertion member, the sleeve 4 axially opens to a greater diameter than the diameter of the wire 5, thus providing a communication between the internal space of the sleeve 4 and the catheter 3. The other end 4a of the sleeve 4 is formed with an aperture 4d which is slightly greater than the diameter of the wire 5, and through which the wire 5 extends. In this manner, the sleeve 4 is slidable around the wire 5. Adjacent to the distal end 5b, the wire 5 is formed with a hemispherical projection 5a while the end 4a of the sleeve 4 is formed with a slit-like groove 4b which provides a communication between the aperture 4d and the exterior, as indicated in FIG. 2a. Accordingly, as the sleeve 4 slides relative to the wire 5, the region of the groove 4b deforms in conformity to the configuration of the projection 5a during a movement of the sleeve 4 as the distal end 4a of the sleeve passes over the projection 5a. In other words, the resistance presented to the movement of the sleeve 4 is increased at this time, thus presenting a braking effort though slightly.

As shown in FIG. 2b, the insertion member 6 has a substantially circular cross section, with a slit-like groove 6a extending from the center to the external surface. The groove 6a extends over substantially the full length of the insertion member 6. The groove 6a has a width which is slightly greater than the diameter of the wire 5, whereby the latter is disposed centrally therein. At its proximate end, the insertion member 6 is formed with a chuck 6b, which projects externally of a connector 7. The insertion member 6 is axially slidable, in the direction of an arrow AR1, together with the sleeve 4, and is supported by the catheter 3, whereby it slides through the space between the catheter and the wire 5. Thus, when an operator moves the chuck 6b axially relative to the catheter 3, the insertion member 6 moves to change the position of the sleeve 4.

Intermediate its length, the wire 5 is bent, with its free end 5c passing through a branch 7a of the connector 7 to be coupled to a knob 8.

In actual use of the intra-aortic balloon pump, the sleeve 4 is initially positioned to its retracted position or within the internal space of the catheter 3, and the balloon 1 is previously folded. The absence of the sleeve 4 within the balloon 1 enables the balloon 1 to be folded into a smaller diameter than the catheter 3. At this time, the insertion member 6 is pulled out from the catheter 3, and thus is separated therefrom.

Under this condition, the portion of the intra-aortic balloon pump which is to be inserted into the physical body of a patient, namely, part of the balloon 1 and the catheter 3, can be inserted into the aorta of the patient without requiring a surgical operation since it has a reduced external diameter generally comparable to that of a balloon pump of the percutaneous type. When the balloon pump is inserted into the aorta of the patient, an air injection into the balloon 1 takes place through the connector 7, whereby the balloon 1 which is folded around the wire 5 will be restored to its original configuration shown in FIG. 1. The distal end of the insertion member 6 is then inserted through the opening of the connector 7 and is expelled in the direction of the arrow AR1 while holding the chuck 6b with hand. This moves the sleeve 4 in the same direction. When the sleeve 4 enters the internal space of the balloon 1 and reaches a given position, its distal end 4a moves past the projection 5a formed on the wire, allowing the operator to perceive a temporary braking action through the chuck 6b. If he then further drives the chuck 6b inward until such braking action is removed, the sleeve 4 is positioned in its position of use as illustrated in FIG. 1. Accordingly, while the sleeve 4 itself is invisible to the operator, he is capable of determining whether the sleeve has reached a given position, thus facilitating the positioning operation.

The distal end 4a of the sleeve 4 has been located beyond the projection 5a of the wire as shown in FIG. 1, and hence any attempt to move back the sleeve 4 in a direction opposite to that indicated by the arrow AR1 will be without effect. In this manner, the sleeve 4 is maintained in the position shown in FIG. 1 if any external force of insignificant magnitude is applied thereto. After the sleeve 4 has reached the given position within the balloon 1, the insertion member 6 is withdrawn from the catheter 3 and the connector 7.

A drive tube 9 of a drive unit (not shown, but having a construction as indicated at 30 in FIG. 4a) is connected to the connector 7. A positive and a negative pressure are alternately applied to the tube 9 in synchronism with the movement of the heart of the patient. Thus, a negative pressure is applied to the tube 9 at timing of pulsation of the heart, whereby fluid such as helium gas, for example, received within the balloon 1 is displaced, allowing it to deflate to thereby depress the blood pressure within the aorta to facilitate the pulsating motion of the heart.

When a negative pressure is applied to the tube 9, the fluid within the balloon 1 passes through the multiplicity of apertures 10 formed in the sleeve 4, through the internal space of the sleeve 4, through the space left between the wire 5 and the catheter 3 to be discharged into the tube 9. Considering the configuration of the balloon 1 more specifically, since fluid passages or apertures 10 are uniformly distributed around the full periphery of the sleeve 4, the deflating motion of the balloon 1 takes place a substantially uniform rate for any axial portion thereof, thus eliminating a biased deformation as illustrated in FIG. 3b. If such a biased deformation does occur, what is blocked by the balloon 1 is limited to only a portion of the periphery of the sleeve 4, leaving the remaining fluid passages intact. In this manner, the interruption of all the fluid passages in the balloon is prevented, thus preventing any retardation in the deflation motion of the balloon 1.

In the described embodiment, the member which carries the distal end of the balloon comprises a metal wire (5), but it may be replaced by a tube of a high density polyurethane or polyethylene (such material avoiding the coagulation of the blood) with the distal end of the tube opening into the distal end of the balloon. An injection of medicine into the physical body of the patient can take place in this manner through the tube.

In the embodiment, the sleeve member comprises a tubular member having a multiplicity of apertures formed therein, but it may be replaced by a metal meshwork which is formed into a tubular configuration. The only requirement is that the sleeve member is movable between a given position within the balloon and the retracted position away therefrom and has the construction which prevents its blockage of a fluid channel formed therein if the balloon undergoes a deflating motion.

In the embodiment, a movement of the sleeve member has been accomplished by coupling a rod-shaped insertion member (6) to one end of the sleeve member, but any alternate means may be provided which is able to displace the sleeve member. Also, in the embodiment, means (projection 5a) which is utilized to recognize the position of the sleeve member has been located adjacent to the distal end of the balloon, but it may be located at other locations.

As described, in accordance with the invention, any interference with the deflating motion of the balloon is eliminated, thus reducing the length of time required for the deflating motion. Since the balloon may be constructed to exhibit a reduced diameter, it may be inserted into the physical body of a patient without requiring a surgical operation.

What we claimed is:

1. An intra-aortic balloon pump comprising a tube member internally formed with a passage for a drive fluid;
    a hollow cylindrical balloon member having two ends, an opening formed at least at one end thereof which is hermetically secured to one end of the tube member;
    a support wire having one end which supports the other end of the balloon member and extending axially through the internal space of the balloon member and through the tube member to be held thereby;
    a sleeve member disposed in surrounding relationship around the support wire and at least partially formed with a fluid passage, the sleeve member being at least partially displaceable in the axial direction with respect to he support wire between a position located within the tube member and a position located in the inside of the balloon member;

and braking means formed on at least one of the support wire and the sleeve member to provide a braking action upon movement of the sleeve member when the latter is located at a given position within the balloon member in which said braking means further includes a means for securing the sleeve member in position when it is located at said given position.

2. An intra-aortic balloon pump according to claim 1 in which the sleeve member is tubular and is formed with a plurality of apertures around its periphery which provide a communication between the internal and external space thereof.

3. An intra-aortic balloon pump according to claim 1 in which the sleeve member has a substantially fixed configuration over its entirety which is less than the external diameter of the tube member.

4. An intra-aortic balloon pump according to claim 1 in which the sleeve member is disposed within the tube member, with a part of the sleeve member extending out of the tube member and further comprising a drive member which is movable axially of the tube member.

5. An intra-aortic balloon pump comprising a tube member internally formed with a passage for a drive fluid;
- a hollow cylindrical balloon member having two ends, an opening formed at least at one end thereof which is hermetically secured to one end of the tube member;
- a support wire having one end which supports the other end of the balloon member and extending axially through the internal space of the balloon member and through the tube member to be held thereby;
- a sleeve member disposed in surrounding relationship around the support wire and at least partially formed with a fluid passage, the sleeve member being at least partially displaceable in the axial direction with respect to the support wire between a position located within the tube member and a position located in the inside of the balloon member;
- and braking means formed on at least one of the support wire and the sleeve member to provide a braking action upon movement of the sleeve member when the latter is located at a given position within the balloon member in which said braking means further includes an opening formed in the sleeve member to pass the support wire therein and a slit-like notch extending from the opening toward the peripheral surface of the sleeve member, and a projection formed on part of the support wire and greater in size than the opening.

6. An intra-aortic balloon pump according to claim 5 in which the sleeve member is tubular and is formed with a plurality of apertures around its periphery which provide a communication between the internal and external space thereof.

7. An intra-aortic balloon pump according to claim 5 in which the sleeve member has a substantially fixed configuration over its entirety which is less than the external diameter of the tube member.

8. An intra-aortic balloon pump according to claim 5 in which the sleeve member is disposed within the tube member, with a part of the sleeve member extending out of the tube member and further comprising a drive member which is movable axially of the tube member.

9. An intra-aortic balloon pump comprising a tube member internally formed with a passage for a drive fluid;
- a hollow cylindrical balloon member having two ends, an opening formed at least at one end thereof which is hermetically secured to one end of the tube member;
- a support wire having one end which supports the other end of the balloon member and extending axially through the internal space of the balloon member and through the tube member to be held thereby;
- a sleeve member disposed in surrounding relationship around the support wire and at least partially formed with a fluid passage, the sleeve member being at least partially displaceable in the axial direction with respect to the support wire between a position located within the tube member and a position located in the inside of the balloon member;
- and braking means formed on at least one of the support wire and the sleeve member to provide a braking action upon movement of the sleeve member when the latter is located at a given position within the balloon member in which said braking means further includes a means for securing the sleeve member in position when it is located at said given position and
- in which said braking means includes an opening formed in the sleeve member to pass the support wire therein and a slit-like notch extending from the opening toward the peripheral surface of the sleeve member, and a projection formed on part of the support wire and greater in size than the opening.

10. An intra-aortic balloon pump according to claim 9 in which the sleeve member is tubular and is formed with a plurality of apertures around its periphery which provide a communication between the internal and external space thereof.

11. An intra-aortic balloon pump according to claim 9 in which the sleeve member has a substantially fixed configuration over its entirety which is less than the external diameter of the tube member.

12. An intra-aortic balloon pump according to claim 9 in which the sleeve member is disposed within the tube member, with a part of the sleeve member extending out of the tube member and further comprising a drive member which is movable axially of the tube member.

* * * * *